United States Patent [19]
Toedtli et al.

[11] Patent Number: 5,185,639
[45] Date of Patent: Feb. 9, 1993

[54] FIBER SAMPLE HOLDER

[75] Inventors: Sergej Toedtli, Wollerau; Alfred Beeler, Horgen, both of Switzerland

[73] Assignee: Siegfried Peyer AG, Wollerau, Switzerland

[21] Appl. No.: 651,401

[22] PCT Filed: May 14, 1990

[86] PCT No.: PCT/CH90/00128
  § 371 Date: May 26, 1991
  § 102(e) Date: May 26, 1991

[87] PCT Pub. No.: WO91/00518
  PCT Pub. Date: Jan. 10, 1991

[30] Foreign Application Priority Data

Jun. 30, 1989 [CH] Switzerland ............ 2438/89

[51] Int. Cl.⁵ .................. G01N 33/36; G01N 1/28
[52] U.S. Cl. .................. 356/245; 73/159; 356/238
[58] Field of Search ........... 356/238, 429, 245, 242; 250/571; 73/159, 160

[56] References Cited

U.S. PATENT DOCUMENTS 2,299,983 10/1942 Hertel ................. 356/245
3,591,294 7/1971 Neil .................... 356/429
3,739,183 6/1973 Burton et al. ........... 356/238

FOREIGN PATENT DOCUMENTS 909677 10/1962 United Kingdom.

OTHER PUBLICATIONS

Soviet Inventions Illustrated. week 88/32, Jul. 14, 1988, Derwent Publications Ltd. (London, GB), abstract No. 88-226823/32 F04503 & SU, A, 1368783 (Ivan Textile Inst.) Jan. 23, 1988.

Textil-Praxis, No. 4, Apr. 1959, M. Hoffmann: "Das Cottonometer, ein neues deutsches Faserlängenmesserät" pp. 332-334.

Textil-Praxis, vol. 27, No. 9, Sep. 1972, M. Preysch: "Neuentwicklungen der Digital Fibrogaphen und ihre Anwendung in der Baum wollspinnerei", pp. 519-524.

Primary Examiner—Richard A. Rosenberger
Attorney, Agent, or Firm—McAulay, Fisher, Nissen, Goldberg & Kiel

[57] ABSTRACT

In a process for preparing and fixing samples of fibres to be analysed optically, a plurality of fibres (5) to be analysed is laid on a first transparent plate (2), the first plate (2) and the fibres (5) lying on it are covered by a second transparent plate (1) and the two plates (1,2) are pressed together and simultaneously displaced coplanarly with respect to each other to form a fixed sample composed of parallel, longitudinally aligned fibres (5).

9 Claims, 1 Drawing Sheet

FIBER SAMPLE HOLDER

BACKGROUND OF THE INVENTION

1. Field of the Invention

The invention is directed to a method for preparing and fixing fiber samples to be analyzed optically and to a device for implementing the method.

2. Description of the Prior Art

There are numerous methods and apparatuses for the qualitative and quantitative optical testing of textile fibers. In many test procedures, the irregular fiber material, e.g. cotton flock, cannot be measured immediately, but rather must first be prepared in fiber bands with a parallelized fiber position. Fiber tufts are removed from such fiber bands, which are parallelized beforehand, to serve as a pattern for test devices which require fibers with parallelized fiber position as test material, e.g. optical scanners and image data analysis devices.

Mechanized devices for producing such fiber bands are already known, e.g. according to the Swiss Patent Application No. 01 468/89. The fiber tufts are then produced with commercially available devices, e.g. type FL100/101 or the "Fibrosampler" from the firm of Spinlab.

However, the problem with such devices consists in fixing the fiber samples produced by these devices in their parallelized alignment and distribution in an unchangeable manner up to the point of their actual measurement, but also subsequent to this in order to carry out control or reference measurements.

According to the prior art, e.g. as described in TEXTIL-PRAXIS 1959, issue 4, pages 332–334 "The Cottonometer, a new German fiber length measuring device" [Das Cottonometer, ein neues deutsches Faserlängenmessgerät], the fiber tufts produced with the various devices are inserted in a plexiglass sleeve by hand without special fastening by means of an insertion fork. The disadvantage in this method consists in that the fibers are in an undefined, curled state and the parallelism depends to a great extent on the care of the operator. Moreover, a relatively large quantity of fibers is necessary in order for the fiber sample to be manually transportable at all.

SUMMARY OF THE INVENTION

The present invention seeks to provide a remedy for this. The object of the invention is to provide a method for preparing and fixing fiber samples to be analyzed optically, which method guarantees permanent and certain findings and rules out subsequent changes in the reciprocal position and distribution of the fibers.

The invention meets this object by means of a method comprising placing fibers on a first transparent plate, and while sliding a second transparent plate over the first plate, effecting fixed longitudinal alignment of the fibers. The device for implementing the method which comprises a first optically transparent plate having lateral guides and a second optically transparent plate which slides within the lateral guides.

The advantages achieved by the invention substantially consist in that, as a result of the method according to the invention, the fibers in the fiber tuft are parallelized and stretched in a reproducible manner by means of the constant contact pressure forces and it is possible to preserve the fiber samples in a permanent and reliable (short- and long-term) manner, wherein the fixed fiber sample can easily be directly optically analyzed without further manipulation, even for fiber samples which contain a very small number of fibers.

An embodiment example of the invention which simultaneously explains the principle of operation is shown in the drawing and explained in more detail in the following.

DESCRIPTION OF THE PREFERRED EMBODIMENTS

Figure 1:
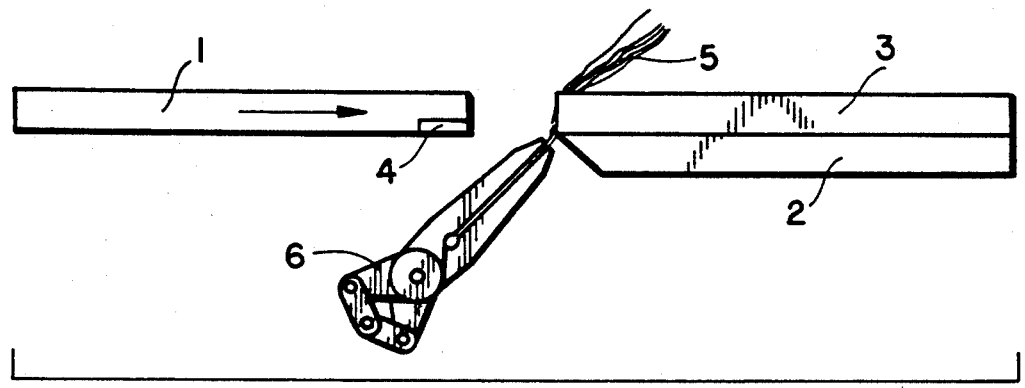
FIG. 1 shows a longitudinal section through a device for implementing the method, according to the invention, in the opened state.

The charging process of the device, according to the invention, is shown schematically in FIG. 1. A plurality of fibers 5 to be analyzed is placed on a first glass plate 2 by means of a pincerlike clamping device 6. A second glass plate 1 is now guided into the lateral guides 3 of the glass plate 2 in the direction of the arrow proceeding from the left-hand side; in so doing, the free ends of the fibers 5 held by the clamping device 6 are clamped in between the two glass plates 1, 2.

When pushing the glass plate 1 into the lateral guides 3 of the glass plate 2, the clamped-in fibers 5 are stretched, parallelized and aligned, and the fibers and dirt particles not held by the clamping device are separated out.

After completely pushing in the glass plates 1, 2, the clamping device 6 is opened in order to release the extremities of the fibers 5, which have been secured until this point, in order to make subsequent use of the sample.

Figure 2:
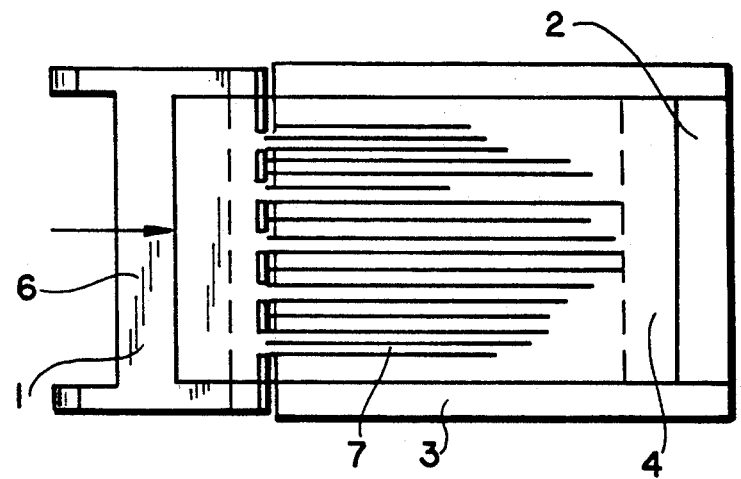
FIG. 2 shows a frontal view of the device according to FIG. 1 during the aligning process.

The resilient and non-destructive clamping of the fibers 5 is enabled by means of a belt 4, e.g. consisting of velvet, felt or foam material, which is attached to the front edge of the second glass plate 1 and additionally serves as a comb for aligning the fibers 5 during the relative displacement of the two glass plates 1, 2 shown in FIG. 2. In order to achieve the desired alignment and parallelism, there must be a minimum contact pressure force between the two glass plates 1, 2, which can be empirically determined. A longitudinal alignment of the fibers 5 to form a parallel, fixed fiber sample 7 which can be directly analyzed as a result of the optical transparency of the two glass plates 1, 2 is accordingly achieved, so that the risk of a change in the relative position of the fibers 5 can be ruled out.

The lateral guides 3 of the first glass plate 2 serve not only for the lateral guidance of the second glass plate 1 during the aligning process, but can also be designed to produce the required contact pressure force, e.g. by means of arranging springs (not shown) which press the two glass plates 1 and 2 together.

Figure 3:
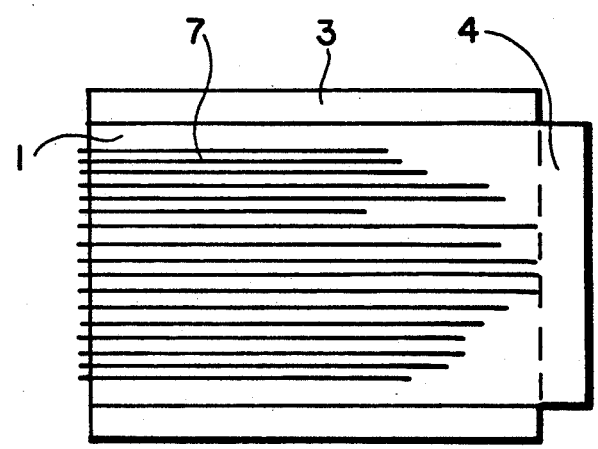
FIG. 3 shows a frontal view of the device according to FIG. 1 in the closed state.

But the belt 4 can also be used to produce the required contact pressure force, e.g. by means of a slight overdimensioning as shown in FIG. 1. The belt 4 is accordingly compressed after successfully introducing the glass plate 1 into the lateral guides 3 of the glass plate 2 and exerts a corresponding pressure on the clamped in fibers 5. Finally, the slightly overdimensioned belt 4 serves to secure the device, according to the invention, after successfully producing the parallelized fiber sample 7, as is shown in FIG. 3; after passing over the right-hand edge of the glass plate 2, the belt 4 expands again and thus prevents the glass plate 1 from being moved back to the left again. For this purpose, the second glass plate 1 is dimensioned so as to be somewhat longer than the first glass plate 2, preferably by an amount corresponding to the belt 4. In order to achieve an optimal fixing, the overdimensioned belt 4 should no longer contact the glass plate 1. The cleaning of the belt 4 can be effected in the closed position of the glass plates and 2.

We claim:

1. A method for preparing and fixing fiber samples to be optically analyzed, the fibers having first and second ends, said method comprising the steps of:
   (a) securing the first ends of the fiber samples;
   (b) placing the second ends on a first optically transparent plate; and,
   (c) pressing a second optically transparent plate against said first plate and simultaneously sliding said plates with respect to each other until said second plate substantially covers said first plate so as to longitudinally align the fibers for forming a parallel, fixed fiber sample.

2. The method of claim 1 further comprising the additional step of releasing the first ends of said fiber samples after the fibers are made parallel and fixed.

3. A device for preparing and fixing fiber samples to be optically analyzed, comprising:
   (a) clamping means for gripping the first ends of the fiber samples;
   (b) a first optically transparent plate;
   (c) guiding means attached to said first plate; and,
   (d) a second optically transparent plate, slidable with respect to said first plate using said guiding means, said second plate comprising aligning means for aligning the fibers parallel to one another.

4. The device of claim 3, said second plate having a front edge, said aligning means comprising a resilient material attached to said front edge.

5. The device of claim 4, said resilient material being selected from the group of materials consisting of velvet, felt, and foam.

6. The device of claim 4, wherein said first plate has a front edge, said second plate is longer than said first plate, and said aligning means has a trailing edge, said trailing edge contacting said front edge when said device is in a closed position, said contact between said trailing edge and said front edge preventing said second plate from sliding down above said first plate.

7. The device of claim 3, wherein said first and second plates are glass.

8. The device of claim 3, wherein said guiding means create a contact pressure between said first and second plates, said pressure fixing the fibers between said first and second plates.

9. The device of claim 8, wherein said aligning means create a contact pressure between said first and second plates, said pressure fixing the fibers between said first and second plates.

* * * * *